(12) United States Patent
Whiston et al.

(10) Patent No.: US 7,772,293 B2
(45) Date of Patent: Aug. 10, 2010

(54) IONIC LIQUID SOLVENTS AND A PROCESS FOR THE DEPOLYMERIZATION OF POLYAMIDES

(75) Inventors: Keith Whiston, Darlington (GB); Stewart Forsyth, Belfast (IE); Kenneth R. Seddon, Donaghadee (IE)

(73) Assignee: Invista North America S.A.R.L., Wilmington, DE (US)

( * ) Notice: Subject to any disclaimer, the term of this patent is extended or adjusted under 35 U.S.C. 154(b) by 85 days.

(21) Appl. No.: 12/182,396

(22) Filed: Jul. 30, 2008

(65) Prior Publication Data

US 2009/0036602 A1    Feb. 5, 2009

Related U.S. Application Data

(60) Provisional application No. 60/952,930, filed on Jul. 31, 2007.

(51) Int. Cl.
*C08J 11/10*    (2006.01)

(52) U.S. Cl. .................................................. 521/40
(58) Field of Classification Search ............... 524/127, 524/156; 521/40
See application file for complete search history.

(56) References Cited

U.S. PATENT DOCUMENTS 7,550,520 B2 *  6/2009  Daly et al. ................ 523/300
2005/0288484 A1 * 12/2005  Holbrey et al. ............. 528/480

OTHER PUBLICATIONS

Org. Lett., 9 (13), 2533-2535, 2007 (Akio Kamimura and Shigehiro Yamamoto; "An Efficient Method to Depolymerize Polyamide Plastics: A New Use of Ionic Liquids".

* cited by examiner

*Primary Examiner*—Peter Szekely

(57) ABSTRACT

An improved process for the hydrolysis of nylon polymer is herein disclosed using ionic liquids and optionally one equivalent of sulfuric acid per amide residue of the polymer. The process provides for a simplified means for separation of the hydrolyzed polyamide constituent monomers.

18 Claims, No Drawings

IONIC LIQUID SOLVENTS AND A PROCESS FOR THE DEPOLYMERIZATION OF POLYAMIDES

FIELD OF THE INVENTION

The invention relates to ionic liquid (IL) solvents having improved properties and more particularly to the use of ionic liquid solvents in a process for the depolymerization of polyamides.

BACKGROUND OF THE INVENTION

It is known to use depolymerization processes in the treatment of waste plastics. A substantial goal of such treatments to plastic waste is chemical recycling. In such a recycle process the waste plastics are converted into constituent monomers which may be suitable for reforming original plastic. In such recycling processes, it is desirable to improve the efficiency of the depolymerization of the waste polymers into their corresponding monomers. Generally, known depolymerization methods involve high-temperatures, high-boiling solvents and often vessels able to withstand high pressures. Solvents used in depolymerization may also include supercritical water or methanol which may require the use of special vessels and pressure handling apparatus.

Polyamides of substantially aliphatic composition, hereinafter nylon, are known to be depolymerized through acid hydrolysis. Such a depolymerization process uses an excess of sulfuric acid, which also functions effectively as the solvent for the process. In order to recover the monomeric materials, a separation or neutralization step is required from the sulfuric acid solvent in which the reaction takes place. The disadvantages of such processes are that they give rise to the generation of significant amounts of problematic effluent streams, and they are also associated with difficulties in the separation and isolation of the target monomers. The products of acid hydrolysis are amine salts and carboxylic acids. In the case of the commercially important polyamide nylon 6,6 (N66), depolymerization would result in the regeneration of the monomers hexamethylene diamine (HMD) and adipic acid (AA).

Recently, ionic liquids (IL) have achieved renewed interest as solvents due to their unique properties. ILs are known for their nonvolatility and stability at high temperature making them suitable for consideration in a low emission recycling system. A recent report of the use of ILs in the depolymerization of polyamides was published in Org. Lett., 9 (13), 2533-2535, 2007 (Akio Kamimura and Shigehiro Yamamoto; "An Efficient Method To Depolymerize Polyamide Plastics: A New Use of Ionic Liquids") and reports a process for the treatment of nylon 6 in an ionic liquid at 300° C. resulting in depolymerization of the polyamide to provide the corresponding monomer, caprolactam, which is collected by direct distillation of the reaction mixture. These authors reported that N-methyl-N-propylpiperidinium bistriflimide (bistrifluoromethylsulfonylimide) provided the best results for the depolymerization of nylon 6 and that the IL could be repeatedly used (ca. five times) without significant decomposition. There is no disclosure of the depolymerization of nylon 6,6.

SUMMARY OF THE INVENTION

The applicant's disclosures provide a method for the hydrolysis of a polyamide derived from a diamine and a dicarboxylic acid comprising contacting said polyamide with a hydrophobic ionic liquid solvent-reactant and water to form a mixture.

The method for polyamide hydrolysis may comprise the steps of: contacting a portion of polyamide solute with a portion of tetraalkylphosphonium $(R_4P)_2^{2-}$ chloride solvent and forming a solution and contacting the solution with one equivalent of sulfuric acid $(H_2SO_4)$ and one equivalent of water per equivalent amide present in the polymer and forming a mixture comprising a portion of aqueous sulfate salts and the tetraalkylphosphonium chloride solvent.

The method may be applied to nylon 66 hydrolysis, comprising the steps of: contacting a portion of nylon 66 solute with a portion of ionic liquid comprising a hydrogensulfate anion $(HSO_4^-)$ in the presence of a stoichiometric amount of water at elevated temperature (ca. 100° C.) and forming a mixture comprising adipic acid, the sulfate salt of hexamethylene diamine and the ionic liquid.

DETAILED DESCRIPTION

The applicant's disclosures herein relate to the findings that ionic liquids (IL) can be beneficially applied as solvents in effecting the hydrolysis of nylon 6,6 polymer. These findings can be applied to methods for polyamide hydrolysis in general and to methods to isolate the constitute monomers of a polyamide. In particular the isolation of monomers from diamine and diacid type polyamides is disclosed.

A wide range of IL can be used as solvents for the reaction in combination with 1 equivalent of $H_2SO_4$ and 1 equivalent of water per amide residue present in the polymer. Nylon, an aliphatic diamine and diacid type polyamide polymer, reacts at elevated temperature (e.g. 100° C.) and the resulting amine salts and diacid dissolve in the solvent matrix. The advantage of this embodiment is that excess acid is not required to carry out the reaction. The use of a hydrophobic IL such as a tetraalkylphosphonium chloride, results in a more easily separable mixture of aqueous sulfate salts and IL at the end of the reaction.

Ionic liquids with an acidic anion, such as bisulfate (or hydrogen sulphate; $HSO_4^-$), can itself act as solvent and the effective reagent for the depolymerization of nylon 6,6. BMIM* $HSO_4$ (where BMIM is 1-butyl-3-methylimidazolium), for example, reacts in the presence of stoichiometric water with the polymer at 100° C. forming adipic acid, and a mixture of $(BMIM)_2 SO_4$, HMDA sulfate salt and adipic acid. In this case the IL anion is acidic enough to hydrolyze the amide bond of the polymer. The stoichiometric reagent/solvent function reduces the usage requirement for sulfuric acid in the process.

*BMIM: 1-butyl-3-methylimidazolium

More beneficially, however, tetraalkylphosphonium hydrogensulfate $((R_4P)_2SO_4)$ ionic liquids also act as reagents for the depolymerization of nylon 6,6. In this case, because of the hydrophobic nature of the IL, the resulting reaction product consists of an IL layer of $(R_4P)_2SO_4$ and an aqueous salt layer consisting of HMDA sulfate and adipic acid. Regeneration of the IL can be simply carried out by the addition of 1 equivalent of sulfuric acid. Adipic acid can be recovered through recrystallization of the aqueous phase and HMDA through subsequent base addition to the aqueous layer. As a result, this improved method of nylon hydrolysis uses only one equivalent of sulfuric acid as reagent for the hydrolysis and simplifies the separation of the constituent monomers.

EXAMPLES

In a generally applicable method to hydrolyze nylon using a hydrophobic ionic liquid, the following procedure is used:

to powdered nylon 66 (ca. 2 grams) in a small vessel is added concentrated sulfuric acid (ca. 1.78 grains), along with water (ca. 0.33 grams), and an ionic liquid solvent (ca, 2 grams). The vessel is sealed with a rubber septum and heated in a stemblock to 100° C. with stirring for several hours. The reaction mixture becomes homogeneous upon the completion of hydrolysis. The reaction mixture is washed several times with water. A non-polar organic solvent (e.g. normal hexane) is optionally used to aid separation of the ionic liquid from water. Any solid material remaining is removed by filtration. Solids removed can be identified by proton NMR and expected to be consistent with adipic acid. The aqueous layer also contains adipic acid, as well as, the HMD salt.

The foregoing disclosure constitutes a description of specific embodiments illustrating how the invention may be used and applied. Such embodiments are only exemplary. The invention in its broadest aspects is further defined in the claims which follow. These claims and terms used therein are to be taken as variants of the invention described. These claims are not restricted to such variants but are to be read as covering the full scope of the invention implicit within the disclosure herein.

What is claimed:

1. A method for the hydrolysis of a polyamide derived from a diamine and a dicarboxylic acid comprising contacting said polyamide with a hydrophobic ionic liquid solvent-reactant and water to form a mixture.

2. The method of claim 1 wherein said contact is effected at, or the mixture is heated to, a temperature of from about 20° C. to about 250° C.

3. The method of claim 2 wherein the temperature is from about 30° C. to about 200° C.

4. The method of claim 3 wherein the temperature is from about 50° C. to about 100° C.

5. The method of claim 1 wherein said diamine is hexamethylene diamine and/or said dicarboxylic acid is adipic acid.

6. The method of claim 5 wherein said polyamide is nylon-6,6.

7. The method of claim 5 wherein water is present in the mixture in an amount of one molar equivalent per mole of amide present in the polymer.

8. The method of claim 5 wherein said ionic liquid contains an anion selected from the group consisting of $[HSO_4]^-$ and $[HPO_4]^{2-}$.

9. The method of claim 1 wherein said contact produces an aqueous phase and an ionic liquid phase.

10. The method of claim 9 wherein said aqueous phase comprises the hydrolysis products of said polyamide.

11. The method of claim 10 further comprising separation of the aqueous phase from the ionic liquid phase.

12. The method of claim 11 further comprising isolating the monomeric dicarboxylic acid hydrolysis product from said aqueous phase.

13. The method of claim 12 further comprising isolating the monomeric diamine hydrolysis product or a salt thereof from said aqueous phase.

14. The method of claim 13 wherein said method further comprises the step of contacting the ionic liquid phase with a stoichiometric amount of $[H^+]$ ions, relative to the amount of anion in the ionic liquid, in order to regenerate the ionic liquid solvent-reactant.

15. The method of claim 14 wherein the regenerated ionic liquid solvent-reactant is recovered and provided as a solvent-reactant for the hydrolysis of further polyamide.

16. The method of claim 15 wherein said ionic liquid contains $[HSO_4]^-$ and said method comprises the step of contacting the ionic liquid phase with a stoichiometric amount of $H_2SO_4$, relative to the amount of $[HSO_4]^-$ in the ionic liquid, to regenerate the ionic liquid solvent-reactant.

17. The method of claim 16 wherein said ionic liquid contains $[HPO_4]^{2-}$ and said method comprises the step of contacting the ionic liquid phase with a stoichiometric amount of $H_3PO_4$, relative to the amount of $[HPO_4]^{2-}$ in the ionic liquid, to regenerate the ionic liquid solvent-reactant.

18. The method of claim 1 or 6 wherein said ionic liquid comprises tetraalkylphosphonium ions.

\* \* \* \* \*